United States Patent
Seibold (10) Patent No.: US 9,987,413 B2
(45) Date of Patent: Jun. 5, 2018

(54) INJECTION SYSTEM FOR INJECTION OF A FLUID AND METHOD FOR CONTROL THEREOF

(71) Applicant: Ulrich GmbH & Co. KG, Ulm (DE)

(72) Inventor: Felix Seibold, Ulm (DE)

(73) Assignee: ULRICH GMBH & CO. KG, Ulm (DE)

( * ) Notice: Subject to any disclaimer, the term of this patent is extended or adjusted under 35 U.S.C. 154(b) by 643 days.

(21) Appl. No.: 14/551,197

(22) Filed: Nov. 24, 2014

(65) Prior Publication Data

US 2015/0151039 A1 Jun. 4, 2015

(30) Foreign Application Priority Data

Dec. 3, 2013 (DE) ......................... 10 2013 113 387

(51) Int. Cl.
*A61M 5/168* (2006.01)
*A61M 5/00* (2006.01)
(Continued)

(52) U.S. Cl.
CPC ........ *A61M 5/007* (2013.01); *A61M 5/14228* (2013.01); *A61M 5/16804* (2013.01);
(Continued)

(58) Field of Classification Search
CPC ...... A61M 2205/3331; A61M 5/16804; A61M 5/16854; A61M 5/172; A61M 2205/3355; A61M 1/1039; F02D 31/001
See application file for complete search history.

(56) References Cited

U.S. PATENT DOCUMENTS

| 6,520,930 B2 * | 2/2003 | Critchlow | A61M 5/14546 417/44.2 |
| 6,673,033 B1 | 1/2004 | Sciulli et al. | |
| 6,691,047 B1 * | 2/2004 | Fredericks | A61M 1/3621 128/204.18 |

OTHER PUBLICATIONS

Result of examination Report for German Application No. 10 2013 113 387.8, filed Dec. 3, 2013 (priority application).

* cited by examiner

*Primary Examiner* — Kevin C Sirmons
*Assistant Examiner* — Deanna K Hall
(74) *Attorney, Agent, or Firm* — Paul D. Bianco; Katharine Davis; Fleit Gibbons Gutman Bongini & Bianco PL (57) ABSTRACT

An injector for the injection of a fluid into human or animal bodies with a pump for the conveying of the fluid at a flow rate, and with a control device for the control of the pump and for the setting of a desired flow rate (theoretical flow) of the fluid, and a pressure measurement device coupled with the control device for the recording of the pressure of the fluid conveyed by the pump, wherein a theoretical pressure is specified for the control device. In order, on the one hand, to reliably prevent an exceeding of a pressure hazard in the injection system and, on the other hand, to avoid an unnecessary prolongation of the injection process by a power reduction or a switching off of the drive mechanism, and to increase the throughput of several injection processes carried out with the injector one after the other, provision is made so that the control device compares the pressure of the fluid recorded by the pressure measurement device to the theoretical pressure, and when the theoretical pressure is exceeded over a time period, integrates the chronological pressure course of the pressure recorded by the pressure device over this time period for the determination of a pressure integral, and switches off the pump or operates it (Continued)

with a lower pump power if the determined pressure integral exceeds a prespecified integral limiting value.

20 Claims, 4 Drawing Sheets

(51) Int. Cl.
*A61M 5/172* (2006.01)
*A61M 5/142* (2006.01)

(52) U.S. Cl.
CPC ........ *A61M 5/16854* (2013.01); *A61M 5/172* (2013.01); *A61M 2205/3331* (2013.01)

INJECTION SYSTEM FOR INJECTION OF A FLUID AND METHOD FOR CONTROL THEREOF

FIELD OF THE DISCLOSURE

The disclosure concerns an injector and a method for the control of an injector.

BACKGROUND OF THE DISCLOSURE

From U.S. Pat. No. 6,673,033 B1, injector systems for the injection of a fluid in medicinal injection methods and a method for their control are known, wherein the injector system has a drive mechanism with which a fluid to be injected is placed under pressure and a sensor to record a variable that is proportional to the fluid pressure and comprises a pressure monitoring mechanism, which is connected with the sensor and the drive mechanism and interrupts the injection process if the sensor measures a value of the recorded variable that corresponds to a pressure hazard (pressure hazard limit). In order to prevent the fluid pressure from approaching the pressure hazard limit or from exceeding it, provision is also made in the pressure monitoring mechanism so that the drive output of the drive unit is limited to a prespecified limiting value if the variable proportional to the fluid pressure attains a value that corresponds to a prespecified pressure limit (power limiting pressure), wherein this prespecified power limiting pressure is below the pressure hazard limit. The pressure of the fluid to be injected is thereby either indirectly recorded, for example, via the current of an electric motor of the drive mechanism, or directly via a power or pressure transducer, wherein the direct recording of the fluid pressure via a power or pressure transducer is preferred, because this is more accurate and compensates for any tolerances of the injector system. The pressure monitoring mechanism is set up so that it cancels the parameters that are specified by an operator of the injection system and with which the injection system is to be operated and reduces or completely stops the drive power of the drive mechanism, if the recorded fluid pressure is above the prespecified pressure limit for the power reduction (power limiting pressure) or the pressure hazard (pressure hazard limit). By the power reduction of the drive power when the recorded fluid pressure exceeds the prespecified pressure limit of the power reduction (power limiting pressure), it is possible to prevent the pressure hazard limit from being reached at all. If the pressure hazard limit is, nevertheless, reached or even exceeded, the power supply of the drive mechanism is completely shut down, so as to prevent a rise in pressure and thus a hazard threat to the patient or damage to the injection system.

This known injection system and the method for its control prove to be disadvantageous, however, because brief rises of the fluid pressure, which may appear, for example, with the start of the injection system at the beginning of the injection process, can lead to an unnecessary power reduction of the drive power of the drive mechanism, or with very high, brief pressure peaks, can even lead to a complete turning off of the drive mechanism and thus to an interruption of the injection process. This leads to a prolongation of the injection time, in which the patient is to be supplied with a prespecified quantity (dosage) of the fluid to be injected. With an interruption of the injection process, a testing of the system by the operator and a restart of the injection process are necessary, which likewise leads to an undesired prolongation of the time of the injection process and to a reduction of the throughput with a number of injection processes that are to be carried out with the injection system, one after the other.

SUMMARY OF THE DISCLOSURE

Proceeding from this, the disclosure relates to a generic injector and a method for its control with which, on the one hand, an exceeding of a pressure hazard limit in the injection system can be reliably prevented, and on the other hand, unnecessary prolongations of the injection process can be avoided by a power reduction or a shutting off of the drive mechanism. With the injector and the method for its control, the efficiency and the throughput of several injection processes to be carried out with the injector, one after the other, are to be increased, with simultaneous assurance that a prespecified limiting value for the pressure of the fluid to be injected is not exceeded in the injection system.

Accordingly, an injector and an injector control method are disclosed. Preferred embodiments are also disclosed.

With the injector in accordance with the disclosure, the drive mechanism for the conveying of a fluid to be injected into a human or animal body, at a prespecified flow rate or flow velocity by a pump, is made available. For the adjustment of a desired flow rate (the volume of the fluid to be injected per unit time) or the flow velocity (the speed of the fluid to be injected in the injection system, in particular, into the injection hoses), which can be specified by the operator of the injector, the pump is controlled by a control device. A pressure measurement device for the recording of the pressure of the fluid conveyed by the pump is coupled with the control device.

The operator of the injector specifies to the control device a theoretical pressure of the fluid to be injected in the injection system and the pressure measurement device records the actual pressure (real pressure) of the fluid at a prespecified site in the injection system, wherein the recording of the fluid pressure can take place either directly, for example, by a power or pressure transducer, or indirectly by the recording of a measurement value of a variable that is proportional to the pressure of the fluid in the injection system.

The pressure of the fluid (actual pressure) recorded in this manner is compared to the prespecified theoretical pressure in the control device. If the recorded pressure of the fluid (actual pressure) exceeds the prespecified theoretical pressure during a specific time period, the chronological pressure course of the pressure (actual pressure), recorded by the pressure measurement device, is integrated over this time period in order to determine the pressure integral and the pump is then turned off only if the thus determined pressure integral exceeds a prespecified integral limiting value. The pressure of the fluid (actual pressure), recorded (directly or indirectly) by the pressure measurement device, is therefore integrated over time, if and as long as the detected fluid pressure is above the prespecified theoretical pressure. By the integration of the chronological course of the recorded pressure of the fluid (actual pressure) over the time period in which the recorded pressure is above the theoretical pressure, any pressure peaks that may appear are suppressed. A turning off of the pump takes place only if the pressure integral calculated by the control device exceeds the prespecified integral limiting value. This is regularly the case only if the recorded pressure of the fluid (actual pressure) is above the prespecified theoretical pressure over a longer time period, and for this reason, pressure peaks which may appear briefly and which, as a rule, are not hazardous for the patient, are suppressed and do not lead to a switching off of the pump. In this way, an unnecessary switching off of the pump or a power reduction of the drive mechanism, which would lead to an unnecessary prolongation of the injection process, are avoided.

The prespecified integral value is appropriately calculated and adjusted such that the actual pressure of the fluid in the injection system cannot reach or exceed a possible pressure hazard value. It is thus possible to omit the specification of an upper limiting value for the pressure of the fluid in the injection system that corresponds to a pressure hazard limiting value. For safety reasons, however, it is also possible to specify such an upper limiting value and to adjust the control of the pump so that the pump is switched off if the pressure of the fluid (actual pressure) recorded by the pressure measurement device does not reach or even exceed the upper limiting value that corresponds to a hazard pressure.

For the determination of the pressure integral, the differential pressure between the pressure (actual pressure) recorded by the pressure measurement device and the theoretical pressure is appropriately integrated over the time period in which the recorded pressure (actual pressure) is above the theoretical pressure.

In a preferred embodiment example of the injector in accordance with the disclosure or the control method in accordance with the disclosure, the control device is set up in such a way that it compares the pressure of the fluid (actual pressure) recorded by the pressure measurement device to the theoretical pressure, and when the theoretical pressure is exceeded, reduces the power of the pump until the actual pressure of the fluid (actual pressure) again corresponds to the theoretical pressure. In this way, it is possible to prevent the actual pressure of the fluid in the injection system from being above the theoretical pressure over a longer time period, which, as a function of the prespecified integral limiting value, could lead to a switching off of the pump.

BRIEF DESCRIPTION OF THE DRAWINGS

These and other advantages and features of the disclosure can be deduced from the embodiment example described in more detail below, with reference to the accompanying drawings. The drawings show the following.

DETAILED DESCRIPTION OF THE DISCLOSURE

Figure 1:
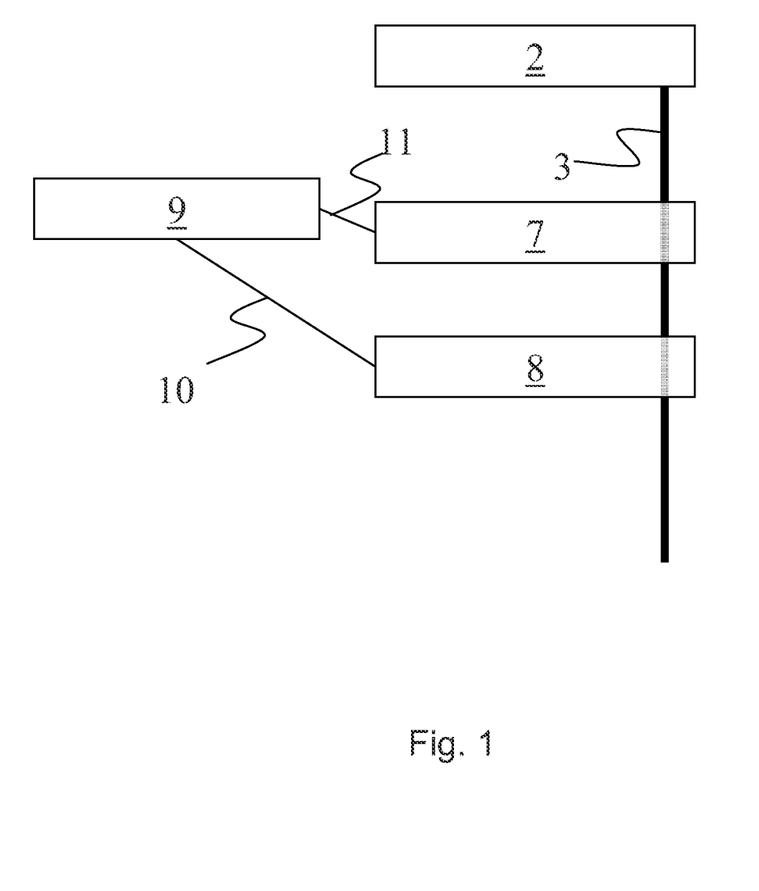
FIG. 1: Schematic representation of the components of an injector in accordance with the disclosure.

In FIG. 1, the components of an injector in accordance with the disclosure are schematically shown in a block diagram. The injector 1 can be used, for example, for the injection of a fluid, in particular, a liquid contrast agent for X-ray or magnetic resonance image-assisted investigations in human or animal bodies. The injection of the fluid to be injected thereby takes place intravenously, as a rule. The fluid to be injected is kept in a fluid reservoir 2. An injection hose 3 is connected to the fluid reservoir 2. The injection hose 3 is coupled with a pump 7. Via the pump 7, the fluid stored in the fluid reservoir 2 is conveyed through the injection hose 3. Preferably, the pump 7 is a hose pump into which the injection hose 3 is placed, so that the hose pump can convey the fluid from the fluid reservoir 2 through the injection hose 3. In this way, it is ensured that the pump does not come into contact with the fluid to be conveyed, which guarantees the sterility of the injection process.

A pressure measurement device 8 is placed downstream from the pump 7 in or on the injection hose 3. Using the pressure measurement device 8, it is possible to record the pressure of the fluid flowing in the injection hose. The pressure measurement device 8 is connected via a data connection 10 to the control device 9. The control device 9 is coupled with the pump 7 via another data connection 11, so as to control the pump 7. The pump 7 is thereby appropriately driven by an electric motor and is electrically controlled via the control device 9. The data lines 10, 11 can be cable-connected or can also be wireless data connections.

The control device 9 appropriately has an input device, which is not depicted here, with which an operator of the injector 1 can input desired parameters (theoretical parameters) for the control of the injection process to be carried out with the injector 1. The operator can specify, for example, a theoretical pressure and a desired flow rate (theoretical flow) of the fluid through the injection hose 3, using the input device. Flow rate is hereby understood to be the volume of the fluid which flows per unit time at a prespecified point (for example, at the end) of the injection hose 3. Alternative to the flow rate (volume per unit time), a flow velocity (flow rate of the fluid) or also a flow density can also be specified. The theoretical values for the pressure and the flow rate of the fluid, input by the input device, are stored in a storage unit of the control device 9, so that a data processing device, which is a component of the control device 9, can access the theoretical values (theoretical pressure and theoretical flow), deposited in the storage unit.

In order to guarantee a correct dosage of the fluid to be injected, the pump 7 is preferably controlled by the control device 9, so that a constant flow rate of the fluid is conveyed via a prespecified injection time period or also via pulsed fluid boluses by the pump 7 through the injection hose 3. As a function of the characteristics and parameters of the pump 7 and the used injection hose 3, it is possible, at various points in time during the injection time, for various pressure values of the fluid conveyed by the pump 7 through the injection hose 3 to form in the injection hose 3. To avoid an excess pressure, the control device 9 controls the pump 7 coupled with it in accordance with the method of the disclosure, which will be explained in detail further below.

Figure 2:
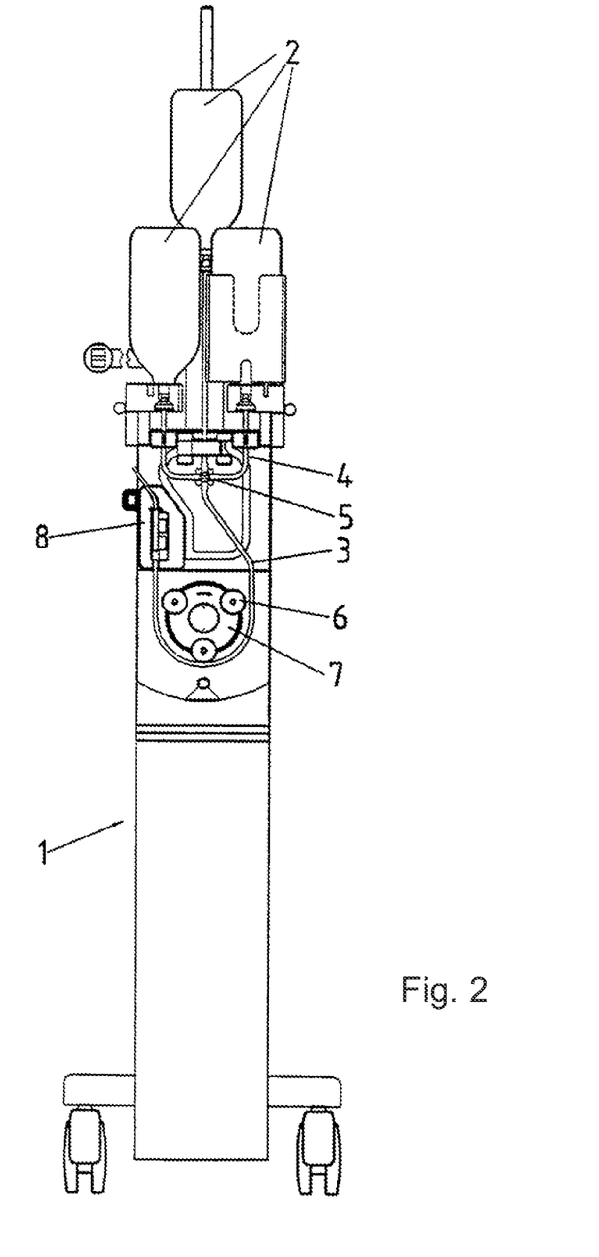
FIG. 2: Front view of a concrete embodiment example of an injector in accordance with the disclosure.

FIG. 2 shows a preferred embodiment example of an injector 1 in accordance with the disclosure in a front view. The injector 1 comprises the fluid reservoir 2, an injection hose 3 connected with the fluid reservoir 2, a pump 7 designed as a hose pump (peristaltic pump), and a pressure measurement device 8 situated on the injection hose 3, downstream from the pump 7, to record the fluid pressure in the injection hose 3. The fluid reservoir 2 is formed by three different supply containers in the embodiment example shown in FIG. 2, which are connected by the shut-off valve or clampable connecting hoses 4 and are connected with the injection hose 3 via a branching piece 5. The fluids to be injected are stored in the supply containers of the fluid reservoir 2. They can thereby be, for example, various contrasting agent liquids and a rinsing solution (for example, a NaCl solution). The shut-off valves in the connecting hoses 4 are thereby appropriately coupled with the control device and can be opened or closed by the control device 9, so that a selection can be made by an operator of the injector 1 via the control device 9 as to which fluid stored in the individual supply containers of the fluid reservoir 2 is to be conveyed through the injection hose 3. The free end of the injection hose 3 appropriately has a standardized hose connection (for example, a Luer connection), via which a patient hose can be connected on the injection hose 3, on whose end an injection cannula is provided, which can be applied intravenously to the patient. The fluid to be injected is then conveyed by the pump 7 through the injection hose 3 and into the patient hose connected to it, and, in this way is injected intravenously to the patient.

The pump 7, designed as a hose pump, has three squeezing rollers 6 and a correlated counter bearing in the embodiment example shown in FIG. 2. The injection hose 3 is placed in the hose pump 7 in such a way that the squeezing rollers 6 press against the injection hose 3 against the counter bearing and in that way, convey the fluid in the hose, while squeezing the hose in a conveying direction with a specifiable flow rate.

Figure 3:
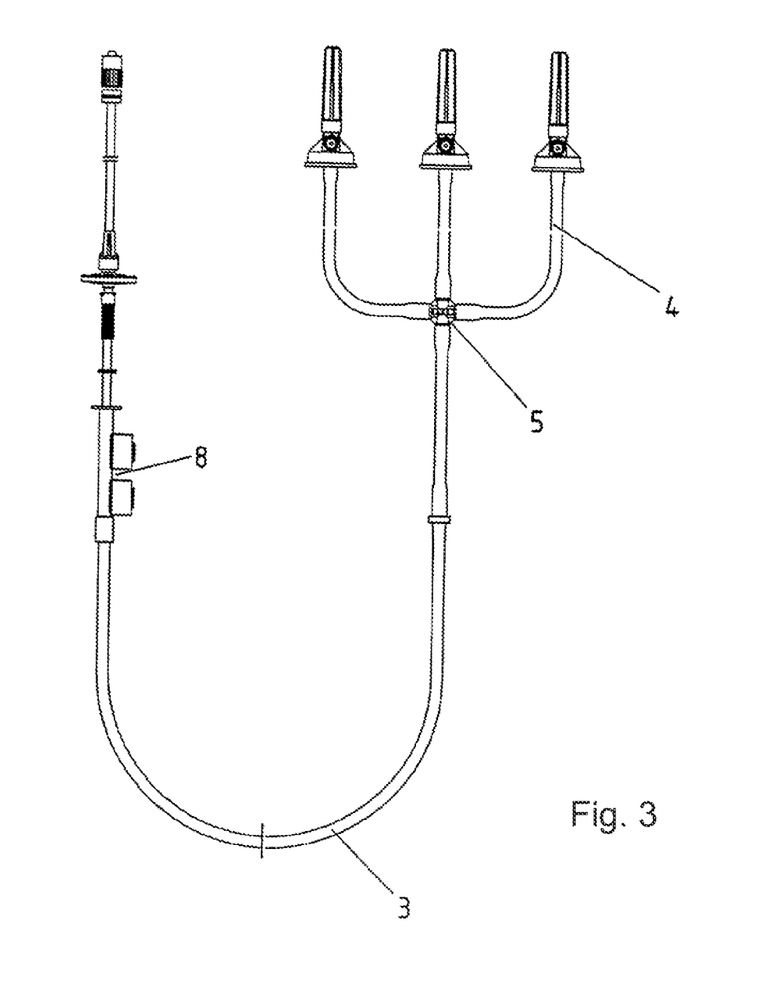
FIG. 3: The hose system used in the injector of FIG. 2, with an injection hose and a pressure measurement device.

The hose system shown in the injector 1 of FIG. 2, with the injection hose 3 and the connecting hoses 4, which are connected via the branching piece 5 with an end of the injection hose 3, is depicted in detail in FIG. 3. The free ends of the connecting hoses 4 are connected with a supply container of the fluid reservoir 2 and the injection hose 3 is, as shown above, introduced into the hose pump. As can also be seen in FIG. 3, a pressure measurement device 8 is located downstream from the pump 7 on the injection hose 3. The pressure measurement device 8 is appropriately a pressure measurement unit with a pressure chamber and a membrane that is coupled with a pressure sensor. The pressure chamber is thereby connected, via openings in the wall of the injection hose 3, with the interior of the injection hose 3, so that the pressure of the fluid flowing in the injection hose 3 is transferred to the pressure chamber and, from there, to the membrane. Via the coupling of the membrane on the pressure sensor, it can record the pressure that prevails in the interior of the injection hose 3 and is produced by the fluid flowing through. The fluid pressure (actual pressure) recorded by the pressure measurement device 8 is sent via the data connection 10 shown in FIG. 1 to the control device 9 and is there evaluated in a data processing device.

The data processing device contained in the control device 9 compares the pressure (actual pressure p) recorded by the pressure measuring device and compares it to the prespecified theoretical pressure that is stored in the data storage unit of the control device 9. As soon as the pressure (actual pressure p) recorded by the pressure measurement device exceeds the prespecified theoretical pressure, the data processing device integrates the chronological pressure course p(t) of the actual pressure (that is, of the pressure p recorded by the pressure measurement device) over the time period $\Delta t = t_2 - t_1$, in which the actual pressure lies above the theoretical pressure. The pressure integral $I(t) = \int p(t) dt$ determined in this manner is constantly compared to a prespecified integral limiting value $I_{max}$ during the time period $\Delta t$ in which the actual pressure is greater than the theoretical pressure. When the thus determined pressure integral I exceeds the prespecified integral limiting value $I_{max}$ stored in the data storage unit of the control device 9 (that is, $I(t) > I_{max}$), the pump 7 is switched off, or at least operated with a lower power, until the pressure (actual pressure p), recorded by the pressure measurement device again corresponds to the theoretical pressure.

Figure 4A:
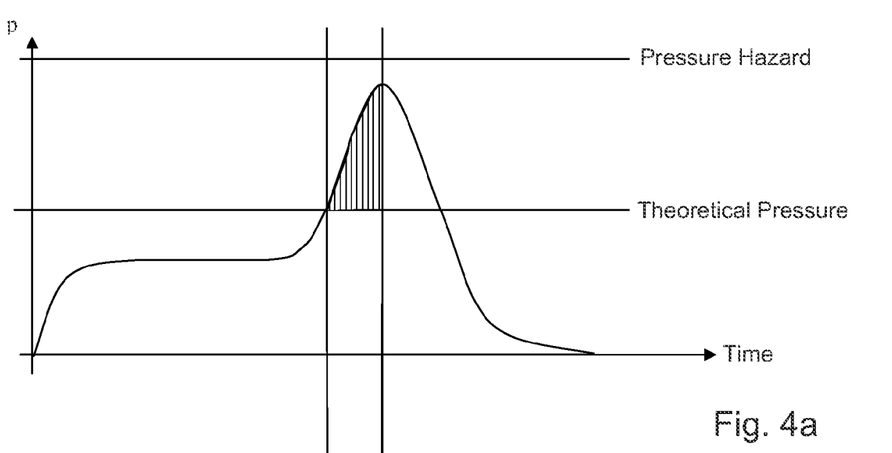
FIG. 4a: Diagram with the chronological course of the pressure of the fluid conveyed in the injection hose of FIG. 3 when carrying out the method in accordance with the disclosure for the control of the injector of FIG. 2.
Figure 4B:
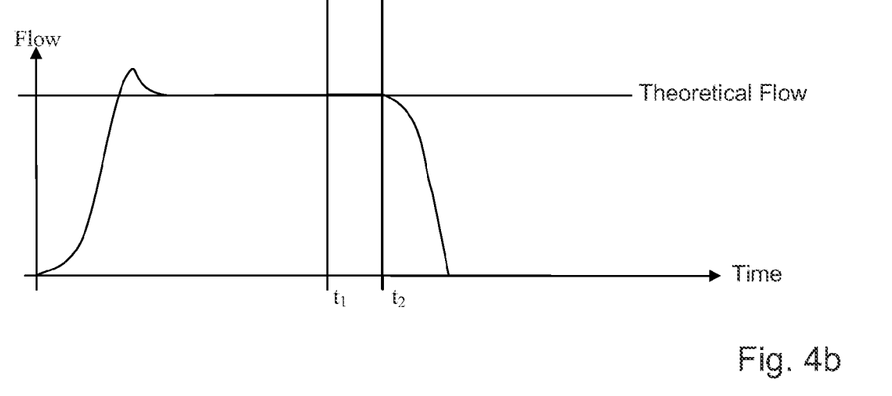
FIG. 4b: Diagram with the chronological course of the flow rate (flow) of the fluid conveyed in the injection hose of FIG. 3 when carrying out the method in accordance with the disclosure for the control of the injector of FIG. 2.

The chronological pressure and flow rate course produced with this control of the injector is depicted in FIGS. 4a and 4b, wherein FIG. 4a shows the chronological pressure course (p(t)) and FIG. 4b, the corresponding chronological course of the flow rate. At the beginning of the injection process (t=0), the pump 7 is switched on and conveys the fluid to be injected from the fluid reservoir 2 through the injection hose 3. The pressure of the fluid in the injection hose thereby rapidly rises until a desired value of the flow rate is reached. The actual flow rate, whose chronological course is shown in FIG. 4b, thereby approximates—as a rule, after a transient peak—the prespecified theoretical flow rate (theoretical flow). The control device 9 appropriately controls the power of the pump 7 in such a way that the actual flow rate corresponds to the prespecified theoretical flow rate (theoretical flow). If, for example, due to a failure of the pump 7 or a clogging in the injection hose 3, a fluid accumulation should be produced that leads to an undesired rise of the actual fluid pressure in the injection hose, the power of the pump 7 is correspondingly reduced or completely shut off in accordance with the disclosure process, so as to avoid a further rise of the fluid pressure, and, in particular, a pressure hazard in the injection hose 3, which could lead to damage in the injector or harm in the tissue of the patient. Such a situation is depicted in the chronological course of the fluid pressure and the flow rate in FIGS. 4a and 4b in the time period $\Delta t$ between the points in time $t_1$ and $t_2$. At the point in time $t_1$, the pressure (actual pressure p) recorded by the pressure measurement device 8 exceeds the prespecified theoretical pressure stored in the data storage unit of the control device 9. As soon as the theoretical pressure is exceeded, the data processing device begins to integrate the chronological course of the actual pressure p(t) as long as the actual pressure lies above the theoretical pressure. The value of the pressure integral I(t) determined by the chronological integration of the actual pressure thereby corresponds to the area under the pressure curve of the chronological course of the actual pressure p(t). Appropriately, as indicated in FIG. 4a, the differential value between the actual pressure p(t) and the prespecified theoretical pressure is integrated over time, so that the determined pressure integral I(t) of the area between the theoretical pressure line and the pressure curve of the actual pressure p(t) corresponds during the time period $\Delta t$, in which the actual pressure p(t) is above the prespecified theoretical pressure. As soon as the thus determined value of the pressure integral I exceeds a prespecified integral limiting value $I_{max}$ stored in the data storage unit, the pump 7 is either completely turned off by the control device 9 or continues to operate only with a lower pump power. In this way, a further rise of the actual pressure is avoided and the chronological course of the actual pressure initially declines to a value below the theoretical pressure, and with a complete shutdown of the pump 7, is, as time goes on, reduced to 0. As soon as the pump 7 is either completely shut down or is operated with a reduced pump power, the actual flow rate also declines, which can be seen in FIG. 4b in the area above the point in time $t_2$. With a complete shutdown of the pump 7, the flow comes to a complete stop and is reduced to 0, as shown in FIG. 4b.

By this control of the pump 7, using the control device 9, it is possible to prevent the actual pressure p(t) from being above the prespecified theoretical pressure over a longer time period. The prespecified theoretical pressure is thereby appropriately selected in such a way that it is far enough below a possible pressure hazard in which there is damage to the injector 1 or its components, or an injury risk to the patient. If the prespecified theoretical pressure is far enough below such a pressure hazard, it is possible to guarantee with sufficient reliability, using the control method in accordance with the disclosure, that the pressure prevailing in the injection hose 3 will not reach the pressure hazard, because the pump 7 will be shut off beforehand, or at least will be operated with a lower power. An additional guarantee of the pump operation with the specification and adjustment of a pressure hazard is possible, but no longer absolutely necessary in the control method in accordance with the disclosure. In particular, with the control method in accordance with the disclosure, one can avoid a switching off or a power reduction of the pump with pressure peaks that appear only briefly, which would not be necessary when avoiding the pressure hazard and therefore would only lead to an unnecessary delay of the injection press. In this way, the throughput of the injector can be increased with the control method in accordance with the disclosure.

The disclosure is not limited to the described embodiment examples. Thus, for example, it is possible to record the pressure of the fluid in the injection hose 3 in another manner, for example, indirectly, via the motor current of the pump 7. Other changes of the injector in accordance with the disclosure and the control method in accordance with the disclosure can be deduced by a specialist using professional knowledge and measures and are included in the scope of protection of the following claims.

The invention claimed is:

1. An injection system for injecting a fluid into a human or animal body, the injection system comprising:
a pump configured for conveying the fluid through the injection system;
a control device configured for controlling the pump and for setting a target flow rate for fluid conveyed through the injection system; and
a pressure-measurement device coupled to the control device and configured for measuring and recording pressure of the fluid conveyed through the injection system;
wherein the control device is further configured for:
comparing the pressure recorded by the pressure-measurement device to a target pressure;
determining if the target pressure is exceeded over a period of time, and if exceeded, integrating a chronological pressure course of the pressure recorded by the pressure-measurement device over the period of time to determine a pressure integral; and
decreasing power to the pump or turning off the pump if the determined pressure integral exceeds a pre-determined integral-limiting value.

2. The injection system according to claim 1, further comprising a fluid reservoir operatively connected to an injection hose.

3. The injection system according to claim 2, wherein the pump is configured for conveying the fluid through the injection system via the injection hose.

4. The injection system according to claim 1, wherein the pump is a hose pump or a peristaltic pump driven by an electric motor.

5. The injection system according to claim 4, wherein the control device is further configured to set a flow rate of fluid conveyed through the injection system at the target flow rate by regulating power supplied to the electric motor driving the pump.

6. The injection system according to claim 5, wherein the control device is configured for regulating power supplied to the electric motor by regulating rpm of the electric motor such that the flow rate is directly proportional to the rpm of the electric motor.

7. The injection system according to claim 1, wherein the control device is further configured for determining the pressure integral by integrating a differential pressure between the pressure recorded by the pressure-measurement device and the target pressure over the period of time.

8. The injection system according to claim 1, wherein the pressure-measurement device is further configured for directly or indirectly measuring pressure of the fluid conveyed through the injection system.

9. The injection system according to claim 1, wherein the pressure-measurement device is further configured for measuring pressure of the fluid at a location within the injection system away from the pump.

10. The injection system according to claim 1, wherein the pressure-measurement device is further configured for measuring pressure of the fluid at a location within the injection system downstream from the pump.

11. The injection system according to claim 1, wherein the control device is further configured for decreasing power to the pump until pressure of the fluid returns to the target pressure.

12. The injection system according to claim 1, further comprising a fluid reservoir operatively connected to an injection hose and wherein the pressure-measurement device is further configured for measuring pressure of the fluid at a location within the injection system downstream from the pump and downstream from the fluid reservoir.

13. An injection system for injecting a fluid into a human or animal body, the injection system comprising:
a pump for conveying the fluid through the injection system;
a control device operatively coupled with the pump via a first data connection, the control device configured for controlling the pump and for setting a target flow rate for fluid conveyed through the injection system; and
a pressure-measurement device positioned downstream from the pump and operatively coupled to the control device via a second data connection, the pressure-measurement device configured for measuring and recording pressure of the fluid conveyed through the injection system;
wherein the control device is further configured for:
comparing the pressure recorded by the pressure-measurement device to a target pressure;
determining if the target pressure is exceeded over a period of time, and if exceeded, integrating a chronological pressure course of the pressure recorded by the pressure-measurement device over the period of time to determine a pressure integral; and
decreasing power to the pump or turning off the pump if the determined pressure integral exceeds a pre-determined integral-limiting value.

14. The injection system according to claim 13, wherein the first and second data connections are configured as wireless data connections.

15. The injection system according to claim 13, further comprising a fluid reservoir having at least two supply containers operatively connected to an injection hose via connection hoses and a branching hose piece.

16. The injection system according to claim 15, wherein a first of the two supply containers includes a contrasting agent and a second of the two supply containers includes a rinsing solution.

17. A method for controlling an injection system for injecting a fluid into a human or animal body, the method comprising steps of:
 setting a target flow rate for fluid conveyed through the injection system;
 setting a target pressure for the fluid conveyed through the injection system;
 activating a pump to convey the fluid through the injection system;
 measuring and recording pressure of the fluid conveying through the injection system;
 comparing pressures measured and recorded over a period of time to the target pressure;
 determining if the target pressure is exceeded over the period of time;
 if the target pressure is determined to be exceeded, integrating a chronological pressure course of the pressure recorded by the pressure-measurement device over the period of time to determine a pressure integral; and
 decreasing power to the pump or turning off the pump if the determined pressure integral exceeds a pre-determined integral-limiting value.

18. The method according to claim 17, wherein the setting of the target flow rate step includes regulating power supplied to an electric motor driving the pump.

19. The method according to claim 17, further comprising a step of determining the pressure integral by integrating a differential pressure between the pressure recorded by the pressure-measurement device and the target pressure over the period of time.

20. The method according to claim 17, further comprising a step of decreasing power supplied to the pump until pressure of the fluid conveying through the injection system returns to the target pressure.

\* \* \* \* \*